(12) United States Patent
Layus et al.

(10) Patent No.: US 11,484,049 B2
(45) Date of Patent: Nov. 1, 2022

(54) ANTIMYCOTOXIN COMPOSITION (71) Applicant: NOLIVADE, Change (FR)

(72) Inventors: Michel Layus, Pleumeur Bodou (FR); Alexandre Brame, Rennes (FR)

(73) Assignee: MIXSCIENCE, Bruz (FR)

( * ) Notice: Subject to any disclaimer, the term of this patent is extended or adjusted under 35 U.S.C. 154(b) by 33 days.

(21) Appl. No.: 16/759,056

(22) PCT Filed: Oct. 31, 2018

(86) PCT No.: PCT/IB2018/058559
§ 371 (c)(1),
(2) Date: Apr. 24, 2020

(87) PCT Pub. No.: WO2019/087110
PCT Pub. Date: May 9, 2019

(65) Prior Publication Data
US 2020/0306321 A1    Oct. 1, 2020

(30) Foreign Application Priority Data
Oct. 31, 2017    (FR) ........................................ 1771150

(51) Int. Cl.
| | |
|---|---|
| *A23L 3/3463* | (2006.01) |
| *A23K 30/00* | (2016.01) |
| *A23K 50/30* | (2016.01) |
| *A23K 10/18* | (2016.01) |
| *A23L 33/135* | (2016.01) |
| *A61P 31/10* | (2006.01) |
| *A23L 3/3571* | (2006.01) |
| *A61K 35/742* | (2015.01) |

(52) U.S. Cl.
CPC ............ *A23L 3/3463* (2013.01); *A23K 10/18* (2016.05); *A23K 30/00* (2016.05); *A23K 50/30* (2016.05); *A23L 3/3571* (2013.01); *A23L 33/135* (2016.08); *A61K 35/742* (2013.01); *A61P 31/10* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 11,213,554 B2 * | 1/2022 | Layus | ................. A61K 35/744 |
| 2013/0045185 A1 | 2/2013 | Davis et al. | |
| 2015/0306154 A1 | 10/2015 | Davis et al. | |
| 2020/0306321 A1 * | 10/2020 | Layus | .................... A23K 10/18 |
| 2020/0353019 A1 * | 11/2020 | Layus | .................... A61P 31/04 |

FOREIGN PATENT DOCUMENTS

WO    WO 2013/178947 A1    12/2013

OTHER PUBLICATIONS

International Search Report dated Dec. 19, 2018 issued in PCT/IB2018/058559.
Gao, Xin et al., "Isolation of Bacillus subtilis: screening for aflatoxins B1, M1, and G1 detoxification", Eur Food Res Technol (2011), vol. 232, pp. 957-962.

* cited by examiner

*Primary Examiner* — Brian Gangle
(74) *Attorney, Agent, or Firm* — Scully, Scott, Murphy & Presser, P.C.

(57) ABSTRACT

The invention relates to the use of a composition comprising at least one strain of *Bacillus subtilis*, for the degradation of mycotoxins.

9 Claims, 4 Drawing Sheets

ANTIMYCOTOXIN COMPOSITION

The invention relates to an antimycotoxin composition.

Mycotoxins are toxins developed by various species of microscopic fungi such as molds (*Aspergillus* sp., *Fusarium* sp., *Stachybotrys* sp., *Penicillium* sp., etc.). These are molecules with low molecular weights (<1,000 daltons), which are most often thermostable in a nonaqueous medium. Poorly degradable, they can remain in foodstuffs even after the elimination of the molds.

Mycotoxins are considered one of the main threats to the food and livestock farming sector worldwide, causing losses of animal productivity of between 2 and 5%.

Preventing the contamination of raw materials by mycotoxins may consist of using fungicides inhibiting mold growth, or the genetic selection of plants resistant to invasion. This is in addition to the care taken during storage (drying, control of the temperature, humidity and oxygenation in silos):

physical methods: washing, drying, grinding, manual or mechanized sorting of pods or kernels, mechanical separation of the shell and the skin, which are the essential contamination location, treatment by thermal shock, roasting, etc.

chemical methods: treatment of peanut oil meals with ammonia. Detoxification with pressurized ammonia lends itself well to the treatment of peanut oil meals or other oleaginous plants arriving by boat;

biological methods such as the addition of a mold inhibitor (propionate) or dilution (amalgam or mixture) of contaminated grains with non-contaminated grains for animal feed (prohibited in some countries).

However, based on current scientific and technical knowledge and despite the improvements made to production and storage techniques, it is not known how to completely prevent mold development. It is likely that this is not possible without using means having more negative side effects, in particular ecologically speaking, but also in terms of health. As a result, the presence of mycotoxins in foodstuffs cannot be completely eliminated. Here, foodstuffs refer to all foods including raw materials, foods intended for humans and foods intended for animals. This presence is also highly dependent on weather conditions, and therefore varies depending on the years.

Furthermore, at this time, it is not possible to eliminate mycotoxins in the preparation of foodstuffs without altering the nutritional value of the products.

The only possible means of prevention is therefore to eliminate "overly" contaminated foods from the food chain. Setting "overly" at the appropriate level is in no way obvious, between the reactions of producers (who inevitably find the standards to be too strict) and safety requirements (which always deem the standards too tolerant). It is known that the higher the requirement level is, the more the costs increase (tests, isolation, elimination or recycling through nonfood channels, etc.) and the less appreciable the health benefit is (relative to a lower, but still effective requirement level).

In the European Union, the most recent standards on mycotoxins are set out by Regulation 1881/2006 setting maximum levels for certain contaminants in foodstuffs and Directive 2002/32/EC on undesirable substances in animal feed.

In parallel, the animal farming sector, and in particular the animal feed industry, are increasingly considered to have a role to play in ensuring the responsible use of antimicrobials in animal production. Decision-makers are asking animal feed producers, farmers, veterinarians and regulating bodies to work together to determine the best farming and hygiene practices and viable alternatives, in order to reduce the use of antibiotics in farm animals and to improve animal well-being. The fight against mycotoxins therefore contributes to this sectoral project by combating pathologies related to mycotoxins, and thus indirectly by decreasing the volumes of antimicrobials used to treat these pathologies.

There is consequently a real need to provide a means to eliminate mycotoxins.

In animal farming, there are multiple current practices to attenuate the risk of mycotoxins, and several solutions are commercially available, such as binders.

Some are not selective enough, and they can therefore quickly be saturated by the food matrices on which they are applied. Likewise, they can interact with nutrients or compounds other than the target mycotoxins, in particular vitamins or minerals. In this case, the bioavailability of these nutrients is reduced as a result.

Others, on the contrary, are too selective, and only provide a solution for one mycotoxin. It is therefore necessary to use strategies combining several solutions to eliminate several mycotoxins present in a same food.

Little data is available at this time on the efficacy of commercially available solutions on foods contaminated below regulatory levels of mycotoxins.

Binders in particular have a known drawback that the mycotoxins still remain present in the food, and therefore in the digestive system of the animal, even if bonded, and may therefore desorb with the proposed solution. Binders can also release accumulated toxic compounds such as heavy metals, dioxins, etc.

Lastly, in the presence of significant mycotoxin contamination, the growth of certain microorganisms may be altered or even inhibited, thus extending the time necessary to reach a satisfactory decontamination level.

The current strategies to combat mycotoxins therefore require building a panel of solutions to eliminate mycotoxins and address these drawbacks.

Patent application US2015306154 is known from the state of the art, and teaches the use of bacteria in the *Bacillus* genus to combat the effects of mycotoxins. However, this document teaches the biotransformation of certain tested mycotoxins and does not appear to provide satisfactory results over all mycotoxins.

Consequently, the need to provide a new method remains.

One aim of the invention is to address these drawbacks.

Another aim of the invention is to propose a new composition that is capable of definitively eliminating mycotoxins contained in foodstuffs and thus improving animal health.

Consequently, particularly proposed is the in vitro or ex vivo use of a composition comprising or consisting essentially of at least one of strains NOL01, NOL02, NOL03 and NOL04, and/or at least one of their metabolites, said strains being deposited at the CNCM under the respective numbers CNCM I-4606, CNCM I-5043, CNCM I-4607 and CNCM I-4608, for breaking down at least one mycotoxin.

The invention in particular relates to the in vitro or ex vivo use of a composition comprising or consisting essentially of at least strain NOL01, and/or of at least one of its metabolites, said strain being deposited at the CNCM under number CNCM I-4606, for breaking down at least one mycotoxin.

The invention in particular relates to the in vitro or ex vivo use of a composition comprising or consisting essentially of at least strain NOL02, and/or of at least one of its metabolites, said strain being deposited at the CNCM under number CNCM I-5043, for breaking down at least one mycotoxin.

The invention in particular relates to the in vitro or ex vivo use of a composition comprising or consisting essentially of at least strain NOL04, and/or of at least one of its metabolites, said strain being deposited at the CNCM under number CNCM I-4608, for breaking down at least one mycotoxin.

The invention in particular relates to the in vitro or ex vivo use of a composition comprising or consisting essentially of at least strain NOL03, and/or of at least one of its metabolites, said strain being deposited at the CNCM under number CNCM I-4607, for breaking down at least one mycotoxin.

The invention is based on the surprising observation made by the inventors that specific strains of bacteria from the *Bacillus subtilis* genus are capable of breaking down several types of mycotoxins produced by the fungi in the medium, without, however, producing toxic residues coming from this breakdown. It has also been observed by the inventors that this decontamination is effective over a wide range of pH, temperature and mycotoxin concentration conditions, and under both aerobic and anaerobic conditions. In the invention, additionally, at least one of strains NOL01, NOL02, NOL03 and NOL04 is used, or the metabolites of these strains, that is to say, molecules secreted by the bacteria, for example enzymes, or at least one of these strains and the metabolites thereof.

In the invention, a strain of bacteria refers to all of the individuals (bacteria) derived from successive subcultures of a bacterial colony.

The metabolites contained in the composition according to the invention are substances secreted by said at least one aforementioned bacterium, and in particular enzymes. In the invention, the aforementioned metabolites can be obtained directly in the culture mediums of strains NOL01, NOL02, NOL03 and NOL04 of *Bacillus subtilis*.

In other words, a strain is a part of the bacterial species that differs from the other bacteria of the same species by a minor, but identifiable difference. A strain is also defined as a population of bacteria that descends from a single organism or the pure isolate culture. The strains of a same species can differ slightly from one another in many respects.

It is advantageous to use the aforementioned composition comprising strain NOL03, where said composition comprises said strain NOL03 deposited at the CNCM under number CNCM I-4607, and at least one of the following strains:
Strain NOL01, deposited at the CNCM under number CNCM I-4606,
Strain NOL02, deposited at the CNCM under number CNCM I-5043, and
Strain NOL04, deposited at the CNCM under number CNCM I-4608.

At least one of strains NOL01, NOL02, NOL03 and NOL04 is used to break down the mycotoxins.

This means that the invention covers the use of the following 15 combinations of strains:
NOL01,
NOL02,
NOL03,
NOL04,
NOL01 and NOL02,
NOL01 and NOL03,
NOL01 and NOL04,
NOL02 and NOL03,
NOL02 and NOL04,
NOL03 and NOL04,
NOL01, NOL02 and NOL03,
NOL01, NOL02 and NOL04,
NOL01, NOL03 and NOL04,
NOL02, NOL03 and NOL04, and
NOL01, NOL02, NOL03 and NOL04.

All of these strains have been deposited in the national collection of microorganisms (CNCM) at the INSTITUT PASTEUR, 25 RUE DU DOCTEUR ROUX, 75724 PARIS CEDEX 15, according to the Budapest Treaty. Strains NOL01, NOLO3 and NOL04 were deposited on Apr. 19, 2012, and strain NOL02 was deposited on Mar. 24, 2016.

Also covered by the invention is the use of one or several of the following metabolites:
One or several metabolites of strain NOL01,
One or several metabolites of strain NOL02,
One or several metabolites of strain NOL03,
One or several metabolites of strain NOL04,
One or several metabolites of strain NOL01 and one or several metabolites of strain NOL02,
One or several metabolites of strain NOL01 and one or several metabolites of strain NOL03,
One or several metabolites of strain NOL01 and one or several metabolites of strain NOL04,
One or several metabolites of strain NOL02 and one or several metabolites of strain NOL03,
One or several metabolites of strain NOL02 and one or several metabolites of strain NOL04,
One or several metabolites of strain NOL03 and one or several metabolites of strain NOL04,
One or several metabolites of strain NOL01 and one or several metabolites of strain NOL02 and one or several metabolites of strain NOL03,
One or several metabolites of strain NOL01 and one or several metabolites of strain NOL02 and one or several metabolites of strain NOL04,
One or several metabolites of strain NOL01 and one or several metabolites of strain NOL03 and one or several metabolites of strain NOL04,
One or several metabolites of strain NOL02 and one or several metabolites of strain NOL03 and one or several metabolites of strain NOL04, and
One or several metabolites of strain NOL01 and one or several metabolites of strain NOL02 and one or several metabolites of strain NOL03 and one or several metabolites of strain NOL04.

If the strains and their metabolites are taken into consideration, the invention therefore covers the following 80 combinations:

| | Strain NOL1 | met NOL01 | Strain NOL2 | met NOL02 | Strain NOL3 | met NOL03 | Strain NOL4 | met NOL04 |
|---|---|---|---|---|---|---|---|---|
| 1 | + | | | | | | | |
| 2 | | + | | | | | | |
| 3 | | | + | | | | | |
| 4 | | | | + | | | | |
| 5 | | | | | + | | | |
| 6 | | | | | | + | | |
| 7 | | | | | | | + | |
| 8 | | | | | | | | + |
| 9 | + | | + | | | | | |
| 10 | + | | | + | | | | |
| 11 | + | | | | + | | | |
| 12 | + | | | | | + | | |
| 13 | + | | | | | | + | |
| 14 | + | | | | | | | + |

-continued

| | Strain NOL1 | met NOL01 | Strain NOL2 | met NOL02 | Strain NOL3 | met NOL03 | Strain NOL4 | met NOL04 |
|---|---|---|---|---|---|---|---|---|
| 15 | + | + | | | | | | |
| 16 | + | | + | | | | | |
| 17 | + | | | + | | | | |
| 18 | + | | | | + | | | |
| 19 | + | | | | | + | | |
| 20 | + | | | | | | | + |
| 21 | | | + | + | | | | |
| 22 | | | + | | | + | | |
| 23 | | | + | | | | + | |
| 24 | | | + | | | | | + |
| 25 | | | | + | + | | | |
| 26 | | | | + | | + | | |
| 27 | | | | + | | | + | |
| 28 | | | | + | | | | + |
| 29 | | | | | + | + | | |
| 30 | | | | | + | | | + |
| 31 | | | | | | + | + | |
| 32 | | | | | | | + | + |
| 33 | + | + | + | | | | | |
| 34 | + | + | | | + | | | |

| | Strain NOL1 | met NOL01 | Strain NOL2 | met NOL02 | Strain NOL3 | met NOL03 | Strain NOL4 | met NOL04 |
|---|---|---|---|---|---|---|---|---|
| 35 | + | | + | | | | | + |
| 36 | + | | + | | | | | + |
| 37 | + | | | + | + | | | |
| 38 | + | | | + | | + | | |
| 39 | + | | | + | | | + | |
| 40 | + | | | + | | | | + |
| 41 | + | | | | + | | + | |
| 42 | + | | | | + | | | + |
| 43 | + | | | | | | + | + |
| 44 | + | | | | | | + | + |
| 45 | | | + | + | | + | | |
| 46 | | | + | + | | | + | |
| 47 | | | + | + | | | | + |
| 48 | | | + | + | | | | + |
| 49 | | | + | | + | + | | |
| 50 | | | + | | + | | + | |
| 51 | | | + | | + | | | + |
| 52 | | | + | | + | | | + |
| 53 | | | + | | | + | + | |
| 54 | | | + | | | + | | + |
| 55 | | | + | | | | + | + |
| 56 | | | + | | | | + | + |
| 57 | | | | + | + | + | | |
| 58 | | | | + | + | | + | |
| 59 | | | | + | | + | + | |
| 60 | | | | + | | + | | + |
| 61 | | | | | + | + | + | |
| 62 | | | | | + | + | | + |
| 63 | | | | | + | | + | + |
| 64 | | | | | + | | + | + |
| 65 | + | + | + | | + | + | | |
| 66 | + | + | + | | + | | | + |
| 67 | + | + | + | | | | + | + |
| 68 | + | + | + | | | | + | + |
| 69 | + | | | + | + | + | | |
| 70 | + | | | + | + | | + | |
| 71 | + | | | + | | | + | + |
| 72 | + | | | + | | | + | + |
| 73 | | | + | + | | + | + | |
| 74 | | | + | + | | + | + | |
| 75 | | | + | + | | | | + |
| 76 | | | + | + | | | + | + |
| 77 | | | + | | + | + | + | |
| 78 | | | + | | + | + | + | |
| 79 | | | + | | + | | + | + |
| 80 | | | + | | + | | + | + | met: metabolites

As described in the table above, the invention therefore covers many compositions, the strains being able to be associated with their metabolites.

In the invention, breakdown refers to the destruction of the mycotoxins, that is to say, the destruction by breaking of the covalent bonds between all or some of their component atoms such that the final product of the breakdown is one or several other molecules no longer or substantially no longer having the toxic properties, for the animals, of the mycotoxins from which they are derived.

The advantage of the composition according to the invention is that it is capable on the one hand of breaking down and not capturing the mycotoxins, but it is also capable of breaking down several mycotoxins of different natures, that is to say, which have a different structure or chemical formula.

In the invention, in vitro and ex vivo refer to a use that does not take place within a higher animal organism (such as birds, mammals or fish) or human, but does not preclude the possibility of use on microorganisms, plants or fungi.

Advantageously, the invention relates to the aforementioned use, for breaking down at least two mycotoxins with different structures.

The aim of the composition according to the invention is to make it possible, in a single use, to eliminate from a determined environment, not a single mycotoxin, but two, or even 3, 4, 5, 6, 7, 8 or 9, or 10 or more, mycotoxins with different structures or chemical formulas.

More advantageously, the invention relates to the aforementioned use, where said composition comprises $10^4$ to $10^{11}$ bacterial colonies, the bacterial colonies being per mL or g of composition.

In other words, in this advantageous embodiment, if the composition according to the invention is in liquid form, said composition will comprise from $10^4$ to $10^{11}$ bacterial colonies of *Bacillus* per mL of composition, for each of the strains when the composition comprises at least two strains.

In the invention, $10^4$ to $10^{11}$ bacterial colonies means: about $10^4$, about $5 \cdot 10^4$, about $10^5$, about $5 \cdot 10^5$, about $10^6$, about $5 \cdot 10^6$, about $10^7$, about $5 \cdot 10^7$, about $10^8$, about $5 \cdot 10^8$, about $10^9$, about $5 \cdot 10^9$, about $10^{10}$, about $5 \cdot 10^{10}$ or about $10^{11}$ bacterial colonies.

One skilled in the art easily knows how to determine this number of bacteria, in particular by counting, either manually (by using a Malassez counting chamber) or by using an automatic cell counter, or by dilution, then seeding on agar and counting the colonies.

Still more advantageously, the invention relates to the use as previously defined, where the cells of *Bacillus subtilis* are in sporulated form and/or in vegetative form.

This means that if the composition comprises a single strain, this strain can be in sporulated form or in vegetative form or a mixture of sporulated form and vegetative form. Conversely, if the composition comprises at least two strains, these strains can both be in sporulated form, or in vegetative form, or one of them is in vegetative form and the other is in sporulated form, or both are in both vegetative and sporulated form. The same is true when the composition comprises 3 or 4 aforementioned strains.

Advantageously, the invention relates to the aforementioned use, where said mycotoxin is produced by a fungus belonging to the group made up of fungi from the genera *Alternaria, Aspergillus, Byssochkamys, Claviceps, Fusarium, Gibberella, Halosarpheia, Penicillium, Phoma, Pyricularia* and *Verticillium*.

The aforementioned fungi, without being limiting, are capable of producing mycotoxins that can be broken down by the composition according to the invention, that is to say, by the at least four separate strains of *Bacillus subtilis*. One of the advantages of the composition according to the invention relative to the prior art is that the composition is not limited to one mycotoxin, but is capable of breaking down nearly all or all of the mycotoxins.

Advantageously, the invention relates to the aforementioned use, where said mycotoxin is chosen from aflatoxins B1, B2, M1, G1 and G2, toxin T-2, toxin HT-2, deoxynivalenol (or nivalenol), zearalenone, fumonisin B1 and ochratoxin A.

Aflatoxins make up a group of 18 structurally close compounds (an assembly of one coumarin and 3 furans). They are produced by *Aspergillus flavus, Aspergillus parasiticus* and *Aspergillus* nomius. The most common include AFB1, AFB2, AFM1, AFG1 and AFG2.

Toxin T-2 ($3\alpha,4\beta,8\alpha$)-12,13-epoxytrichothec-9-ene-3,4,8,15-tetrol) (4,15-diacetate-8-(3-methylbutyrate) is a mycotoxin from the family of trichothecenes. It is toxic for humans and animals. It is in particular produced by *Fusarium sporotrichioides, Fusarium langsethiae* and *Fusarium poae*.

Toxin HT-2 is a mycotoxin from the family of trichothecenes. It is toxic for humans and animals. It is in particular produced by *Fusarium sporotrichioides, F. langsethiae* and *F. poae*.

DONs (deoxynivalenol) are produced by various fungal contaminants from the genus *Fusarium* (*F. graminearum, F. culmorum, F. roseum*, etc.) that contaminate grains of wheat, barley, oats or corn and even rice during blooming.

Zearalenone is a mycotoxin produced by certain species of fungi in the soil, *Fusarium*, which may colonize certain plants (in particular grasses), producing a disease therein, fusariosis.

Fumonisin as a family of mycotoxins emitted by certain species of fungi in the soil, *Fusarium* (mainly *F. verticillioides* and *F. proliferatum*), that can colonize certain plants (in particular grasses), producing a disease therein called fusariosis. Several variants are known, including fumonisin B, which is very toxic, and is mostly found in corn. Fumonisins of type B can cause pulmonary edema in pigs, fatal leukoencephalopathy in horses, and it is hypothesized that it may also be a cause of esophageal cancer in humans.

Ochratoxin A is a mycotoxin produced by several fungi (genera *Penicillium* and *Aspergillus*) and which is naturally present in many plant products, such as cereals, coffee beans, cacao and dried fruits. Ochratoxin A is carcinogenic, nephrotoxic, teratogenic, immunotoxic and potentially neurotoxic. It is also associated with nephropathy in humans.

The invention advantageously relates to a method for breaking down mycotoxins contained in a food intended for animal consumption comprising a step for placement in contact with a composition comprising or consisting essentially of at least one of strains NOL01, NOL02, NOL03 and NOL04, and at least one metabolite thereof (molecules secreted by the bacteria, for example enzymes), said strains being deposited at the CNCM under respective numbers CNCM I-4606, CNCM I-5043, CNCM I-4607 and CNCM I-4608, and optionally a step for inactivation after incubation of said strains of *Bacillus subtilis*, in particular by heat.

The invention further relates to a method for decontamination of food, raw material or fodder contaminated by at least one mycotoxin, said method comprising a step for placement in contact of said foodstuff or fodder with a composition comprising or consisting essentially of
    the at least one of strains NOL01, NOL02, NOL03 and NOL04, and/or
    at least one metabolite thereof,
said strains being deposited at the CNCM under respective numbers CNCM I-4606, CNCM I-5043, CNCM I-4607 and CNCM I-4608.

This method makes it possible to decontaminate food products in particular by exposing, under appropriate conditions, foods, raw materials or fodders contaminated with one or several mycotoxins with the aforementioned composition.

The toxins will then be broken down at the end of this decontamination, making said foods, raw materials and fodders suitable for consumption without risk.

Advantageously, the invention relates to the aforementioned method where said food, raw material or fodder is contaminated by at least two mycotoxins with different structures.

In another aspect, the invention relates to a composition comprising or consisting essentially of
    the at least one of strains NOL01, NOL02, NOL03 and NOL04, and/or
    at least one metabolite thereof,
    said strains being deposited at the CNCM under respective numbers CNCM I-4606, CNCM I-5043, CNCM I-4607 and CNCM I-4608,
    for use thereof in the treatment of animals suffering from a pathology related to the ingestion of at least one mycotoxin, or the prevention of said pathologies.

Due to the ability to break down mycotoxins, the aforementioned composition can be used on a preventive basis against diseases or symptoms developed following the ingestion of mycotoxins. Likewise, the composition according to the invention can be administered on a curative basis in animals poisoned by said mycotoxin.

Multiple effects may be developed following the ingestion of mycotoxins, and are for example hepatotoxic, neurotoxic, mutagenic, teratogenic, carcinogenic, immunosuppressive and/or disruptive for the endocrine system.

The bacteria contained in the composition according to the invention can be in sporulated and/or vegetative form. In this form, they can be administered orally (per os) directly via the food, drinking water or medicament (incorporated directly into the mouth of the animal via a syringe).

More advantageously, the invention relates to the composition for the aforementioned use thereof, where the composition comprises from $10^4$ to $10^{11}$ bacterial colonies per mL or per gram of composition.

Advantageously, the invention relates to the aforementioned composition for the aforementioned use thereof, where said pathologies are related to the ingestion of at least two mycotoxins with different structures.

The invention will be better understood upon reading the following example and figures.

EXAMPLES

Example 1—In Vitro Tests

The inventors tested the properties of reducing the mycotoxin concentration of bacterial strains NOL01, NOL02, NOL03 and NOL04 on ZEA (zearalenone).

1—Effect of the Presence of Toxins on Cell Growth

The ZEA toxins used for this test are provided by Sigma-Aldrich (Milan, Italy), the purity of which is greater than 99%. The toxins are dissolved in acetonitrile at 1 mg/mL, then filtered on a filtration tube with 0.2 μm cellulose membrane (RC/G) (LABOCHEM Science S.r.l., ITALY). An appropriate volume of standard ZEA solution is added to the TSB medium to obtain the desired final concentration (1 μg/mL). The different bacterial layers were cultivated in a TSB culture medium in the presence or absence of 1 μg/mL of ZEA at 30° C., with agitation at 150 rpm, under aerobic conditions.

Figure 6:
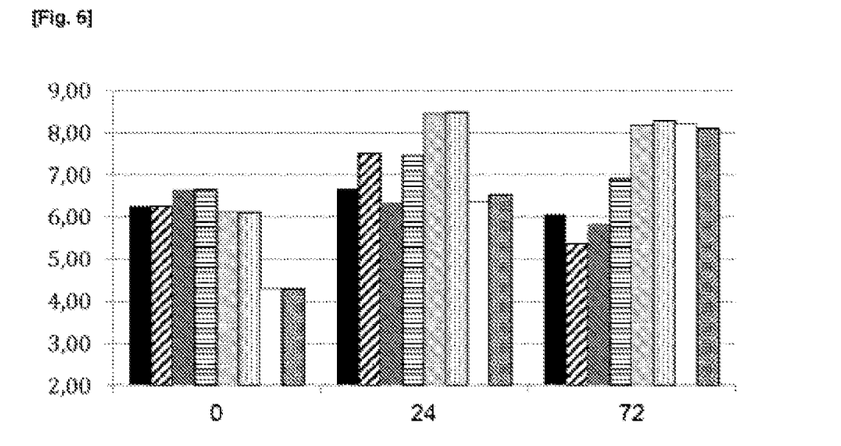
FIG. 6 shows a histogram showing the number of bacteria (log CFU/mL) as a function of time (0, 16 and 72 h) of bacteria NOL01 (black bar), NOL02 (dark gray bar), NOL03 (light gray bar) and NOL04 (white bar) cultivated without ZEA toxins, and bacteria NOL01 (bar with diagonal crosshatching), NOL02 (bar with horizontal crosshatching), NOL03 (bar with vertical crosshatching) and NOL04 (bar with dots) cultivated with 1 μg/ML of ZEA toxin.
Figure 7:
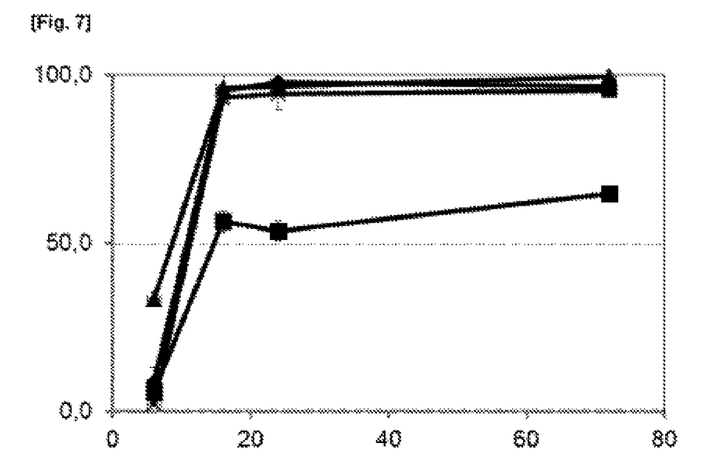
FIG. 7 is a graph showing the percentage of reduction of ZEA toxin over time (in hours) for strains NOL01 (diamonds), NOL02 (squares), NOL03 (triangles) and NOL04 (crosses).
Figure 8:
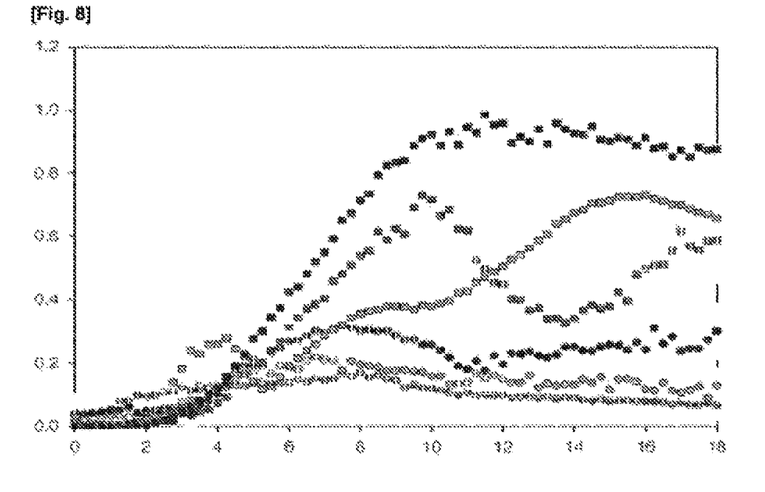
FIG. 8 shows a graph of the growth of the bacteria according to the invention NOL01 (dark gray), NOL02 (light gray) and NOL03 (black) in the presence of ZEA and as a function of the medium: TSB-rich medium (square dot), minimal medium MM (round dot). The x-axis shows the time in hours, and the y-axis shows the absorbance of the solution correlated with the growth of the bacteria ($OD_{600nm}$).

The culture data are shown in FIG. 6. These results show that strains NOL01, NOL02, NOL03 and NOL04 develop as well, or even more quickly in the presence of ZEA at a concentration of 1 μg/mL of medium.

Figure 1:
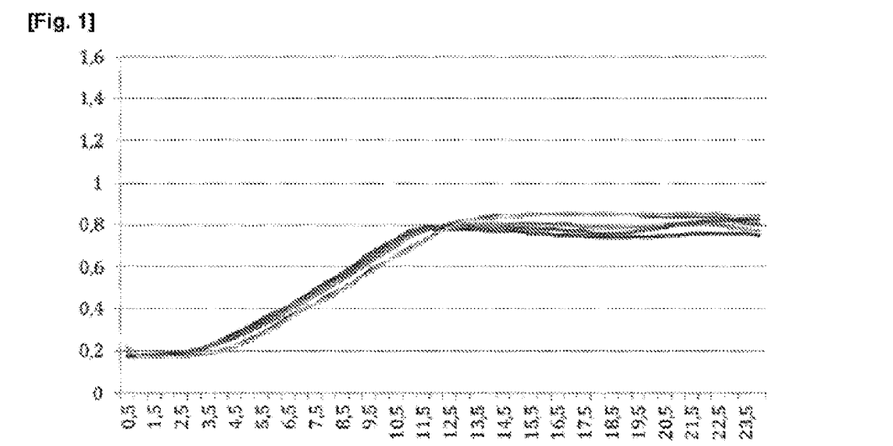
FIG. 1 shows a graph of the growth of NOL01 as a function of different concentrations of ZEA in the medium (0, 0.1, 0.5, 1 and 10 ppm). The x-axis shows the time in hours and the y-axis shows the absorbance of the solution correlated with the growth of the bacteria.
Figure 2:
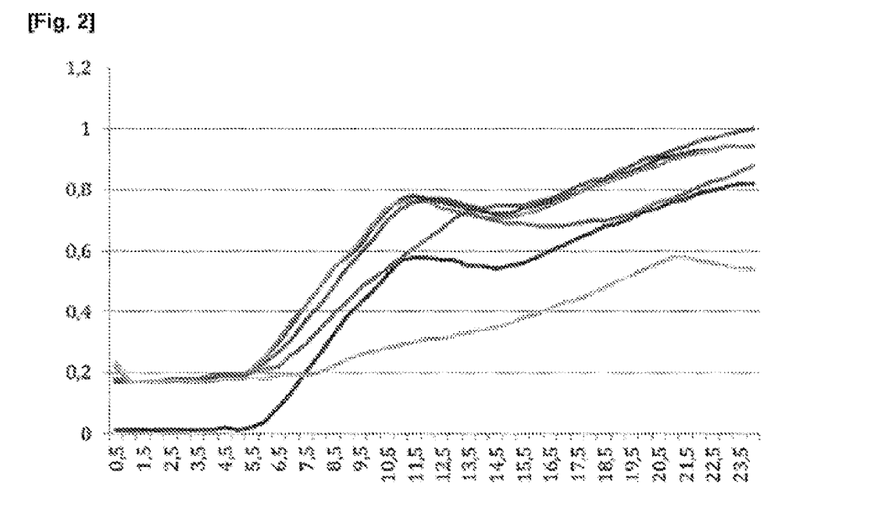
FIG. 2 shows a graph of the growth of NOL02 as a function of different concentrations of ZEA in the medium (0, 0.1, 0.5, 1, 5 and 10 ppm). The x-axis shows the time in hours and the y-axis shows the absorbance of the solution correlated with the growth of the bacteria.
Figure 3:
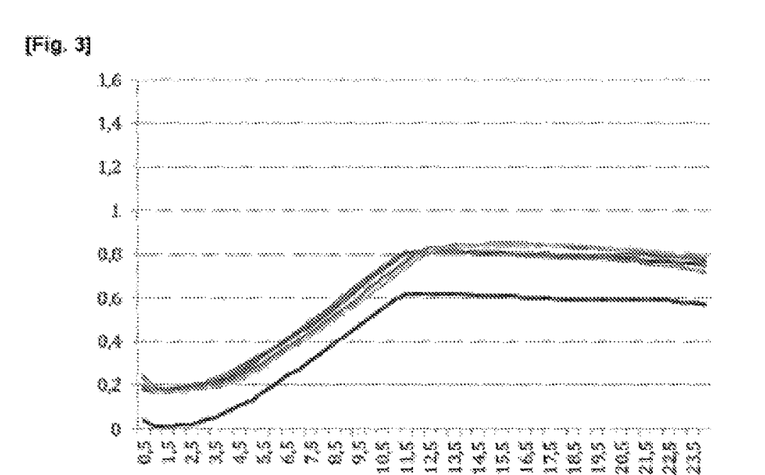
FIG. 3 shows a graph of the growth of NOL03 as a function of different concentrations of ZEA in the medium (0, 0.1, 0.5, 1, 5 and 10 ppm). The x-axis shows the time in hours and the y-axis shows the absorbance of the solution correlated with the growth of the bacteria.

Next, different concentrations of ZEA in the medium were tested, and the results showed that strains NOL01, NOL02 and NOL03 developed equivalently under all tested ZEA concentrations, as shown by FIGS. 1 to 3.

Figure 4:
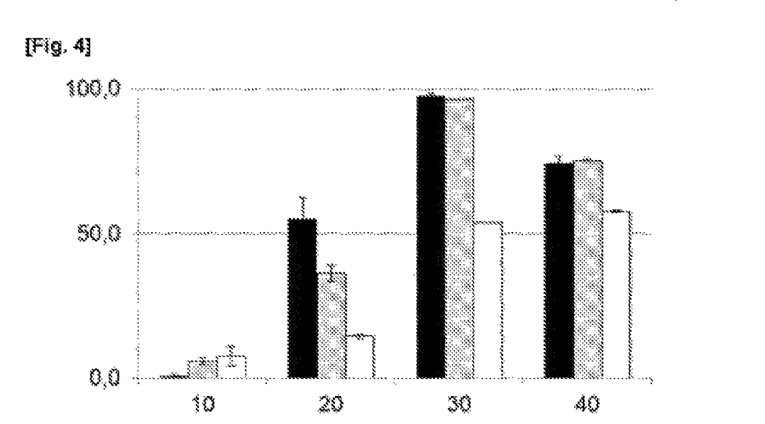
FIG. 4 shows the percentage of breakdown of the ZEA by strains NOL01 (black), NOL02 (white) and NOL03 (gray) as a function of the temperature in degrees Celsius.
Figure 5:
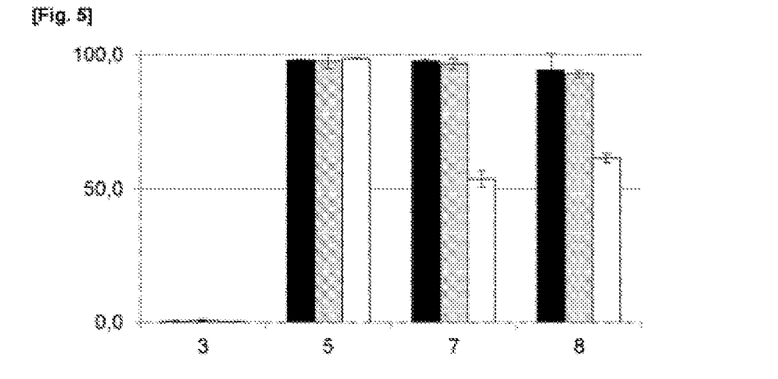
FIG. 5 shows the percentage of breakdown of the ZEA by strains NOL01 (black), NOL02 (white) and NOL03 (gray) as a function of pH of the medium.

Lastly, different pH and temperature conditions were also tested. The obtained results show that NOL01, NOL02 and NOL03 have a reduced activity of the ZEA at 10, 20 and 30° C. (FIG. 4) as well as at pH 5, 7 and 8 (FIG. 5).

These results show that the strains of *Bacillus subtilis* of the invention have the ability to develop in the presence of high concentrations of mycotoxins, and that the property of reducing the mycotoxin concentration is preserved under many conditions, in particular pH and temperature.

2—Measurement of the Quantity of Toxins after Culture

After the various aforementioned cultures, the inventors tested the presence of toxins.

In order to measure the quantity of toxin, the inventors used DonTest™ and ZearalaTest™ absorption kits (VICAM/Waters Corporation, Milford, Mass., USA).

0.5 mL of supernatant of each culture is mixed with 1.5 mL of phosphate buffer (PBS) and applied on the corresponding columns for desorption of the toxin, at the speed of one drop per second.

The columns are next washed with 5 mL of distilled water at the same speed.

The toxins are next eluted with 2 mL of methanol, and the eluates are dried at 50° C. The dry products are next transferred into a mixture of 250 μl $H_2O$:MeOH 85:15, before LC mass spectrometry analysis.

For the detection of the ZEA toxin, the inventors used the Agilent 1100 HPLC system device. The conditions are as follows:

analytical column: Phenomenex® PFP (100 mm×4.6 mm, 2.6 μm), 40° C.;

mobile phase: Water+Methanol+Acetonitrile 50+25+25 (v/v/v) ISOCRATIC;

flow rate: 0.800 mL/min;

retention time: 6.7 min;

Fluorescence 274 nm λ(ex) and 440 nm λ(em).

The results obtained for the ZEA toxin are shown in the following table, and in FIG. 3:

TABLE 3

| | Percentage ZEA reduction* | | | |
|---|---|---|---|---|
| time (h) | NOL01 | NOL02 | NOL03 | NOL04 |
| 6 | 8.7 ± 4.6 | 6.0 ± 0.0 | 33.5 ± 1.9 | 2.2 ± 0.1 |
| 16 | 95.5 ± 1.5 | 57.0 ± 3.1 | 96.1 ± 4.2 | 93.2 ± 1.7 |
| 24 | 97.7 ± 0.6 | 53.6 ± 3.0 | 96.6 ± 1.9 | 94.4 ± 4.9 |
| 72 | 96.9 ± 0.6 | 64.8 ± 2.1 | 99.4 ± 1.1 | 95.5 ± 1.0 |

*average of the % obtained over 3 independent studies and standard deviation

These results show an almost total reduction of the ZEA (more than 94%) after 24 h with NOL01, NOL03 and NOL04 and more than 50% for NOL02.

To confirm these results, the inventors repeated the same experiments for the ZEA toxin. The results are indicated in the following table:

TABLE 4

| | Percentage ZEA reduction* | | | |
|---|---|---|---|---|
| time (h) | NOL01 | NOL02 | NOL03 | NOL04 |
| 24* | 97.7 ± 0.6 | 53.6 ± 3.0 | 96.6 ± 1.9 | 94.4 ± 4.9 |
| 24** | 95.7 ± 2.5 | 56.5 ± 2.5 | 91.3 ± 1.4 | 91.8 ± 0.8 |
| Value P | 0.238 | 0.264 | 0.415 | 0.090 |

*average of the % obtained over 3 independent studies and standard deviation

Since the value P is greater than 0.05, the results are considered to be repeatable. *: first series of tests, **: second series of tests.

3—Adsorption Test on Bacteria

The inventors next tested whether the toxins are adsorbed on the bacteria.

To that end, the bacteria cultures after 24 h in the presence of ZEA were treated as follows:

The bacterial pellets are transferred into 1 mL of an acetonitrile:water mixture (90:10; v/v), and the mixtures are agitated vigorously using a vortex, and lastly centrifuged for 20 min at 14,000 G. The obtained supernatants are next dried at 50° C. and the dry residues are transferred into 1 mL of a water:methanol 85:15 v/v mixture for analysis by spectrometry as described in detail above.

The ZEA desorption results are indicated in the following table:

TABLE 5

| Strain | Percentage of desorbed ZEA* |
| --- | --- |
| (NOL01) | 3.2 |
| (NOL02) | 11.9 |
| (NOL03) | 4.0 |
| (NOL04) | 4.4 |

*average of the % obtained over 3 independent studies and standard deviation

These results suggest that, in light of the small quantity of desorbed ZEA, the toxin is either internalized in the bacteria, or broken down by said bacteria.

4—Test for Breakdown by the Bacteria

In order to test the hypothesis of breakdown by the bacteria, the inventors tested the presence of toxin directly in the bacteria.

To that end, from bacteria cultivated for 24 h with 1 µg/mL of ZEA, the bacterial pellets were transferred into 1 mL of an acetonitrile:water mixture (90:10; v/v) and lysed by sonication. The sonication conditions are as follows: probe diameter: 3.175 mm, frequency: 20 kHz, amplitude: 50%, sonication: 15 sec, then stop 15 sec (6 times), sonication duration: 90 seconds total (without pause times), temperature: 4° C.

After sonication, the specimens are centrifuged for 20 min at 14,000 G. The obtained supernatants are next dried at 50° C. and the dry residues are transferred into 1 mL of a water:methanol 85:15 v/v mixture for analysis by spectrometry as described in detail hereinafter. Device: Aquity UPLC® BEH C18 (100 mm×2.1 mm, 1.7 µm)—50° C.; UV absorbance at 220 nm; Fluorescence: 274 nm λ(ex) and 440 nm λ(em). The retention time of the ZEA was 11.5 min.

The ZEA results extracted from the different pellets are as follows:

TABLE 6

| Strain | Percentage of desorbed ZEA* |
| --- | --- |
| (NOL01) | 2.7 |
| (NOL02) | 0.1 |
| (NOL03) | 0.0 |
| (NOL04) | 1.4 |

*average of the % obtained over 3 independent studies and standard deviation

These results show that the ZEA is not detectable, even when the bacteria are lysed, meaning that the mycotoxin is broken down by the bacteria.

5—Culture in Anaerobic Conditions

The Inventors also tested bacterial growth conditions according to 1—, but in the absence of oxygen.

They next measured the breakdown of the ZEA mycotoxin under these conditions, according to the protocols described above.

The results are provided in the following table:

TABLE 7

| Type of incubation | Percentage of ZEA reduction** | | | |
| --- | --- | --- | --- | --- |
|  | NOL01 | NOL02 | NOL03 | NOL04 |
| aerobic* | 97.7 ± 0.06 | 53.6 ± 3.0 | 96.6 ± 1.9 | 94.4 ± 4.9 |
| anaerobic* | 92.9 ± 1.4 | 44.5 ± 5.0 | 92.6 ± 2.8 | 90.3 ± 0.5 |
| Value P | 0.259 | 0.080 | 0.530 | 0.121 |

*the tests were done after 24 h of culture in the presence of 1 µg/mL of mycotoxin
**average of the % obtained over 3 samples of standard deviation These results show that, irrespective of the culture condition (presence or absence of oxygen), the bacteria are capable of breaking down the mycotoxins.

6—Culture in Minimal Mediums

The inventors also tested the bacterial growth conditions according to 1—, but in a minimal medium, that is to say, a depleted, non-enriched medium (MM), without adding carbon other than that provided by the mycotoxins, the composition of which is as follows for 1 L of culture medium:

TABLE 8

| Compound | Quantity |
| --- | --- |
| $K_2HPO_4$ | 2.72 g |
| $KH_2PO_4$ | 1 g |
| $Na_2SO_4$ | 0.284 g |
| $NaNO_3$ | 0.17 g |
| KCl | 0.15 g |
| $CaCl2 \times 6H_2O$ | 22 mg |
| $MnCl_2 \times 4H_2O$ | 15 mg |
| $FeCl_3 \times 6H_2O$ | 2.16 mg |
| $MgCl_2 \times 6H_2O$ | 25 mg |
| $NH_4Cl$ | 1 g |
| Yeast extract | 0.05% |
| Water | Qs |

These results show that the strains of *Bacillus subtilis* of the invention have the ability to develop in a minimal medium MM, even if the growth level is less than in a rich medium TSB.

Following the different aforementioned cultures and additional cultures done according to 1—but in the presence of 20 µg/mL of ZEA in MM medium, in the presence of 1 µg/mL of ZEA under anaerobic conditions in a MM medium, in a minimal medium re-enriched with $NO_3$ (MMN) and in a minimal medium re-enriched with $NO_3$ and glucose (MMNG), the inventors tested the presence of toxins according to 2—at t=72 h.

The results obtained for the ZEA toxin are shown in the following table:

TABLE 9

| Condition | Medium | ZEA | Percentage of ZEA reduction* | | |
| --- | --- | --- | --- | --- | --- |
|  |  |  | NOL01 | NOL02 | NOL03 |
| Aerobic | TSB | 1 µg/mL | 96.9 | 64.8 | 99.4 |
|  | MM | 1 µg/mL | 100 | 100 | 100 |
|  |  | 20 µg/mL | 99.7 | 48.9 | 99 |
| Anaerobic | TSB | 1 µg/mL | 92.9 | 44.5 | 92.3 |
|  | MM | 1 µg/mL | 32.5 | 24.1 | 32.5 |
|  | MMN | 1 µg/mL | 23 | 20.4 | 80.1 |
|  | MMNG | 1 µg/mL | 98.4 | 80.3 | 96.4 |

*average of the % obtained over 3 samples

These results show, under aerobic conditions, a reduction of the ZEA obtained in minimal medium MM comparable to that observed in rich medium TSB, irrespective of the initial ZEA concentration.

Under anaerobic conditions, a same breakdown level of the mycotoxins as in the rich medium TSB is achieved by the three strains according to the invention, tested in minimal medium re-enriched with $NO_3$ and glucose (MMNG). The same finding is reached for NOL03 in minimal medium re-enriched with $NO_3$ (MMN).

These results show that irrespective of the culture medium (rich, minimal or re-enriched minimal), the bacteria according to the invention are capable of breaking down the mycotoxins, with greater efficacy in rich and re-enriched minimal mediums.

7—Reduction of Mycotoxins Other than ZEA

The inventors also conducted bacterial cultures according to the invention according to 1—but in the presence of mycotoxins other than ZEA, then measured the quantity of toxin after culture according to 2—with appropriate absorption kits for each of the tested mycotoxins, at t=72 h.

TABLE 10

| | Percentage of reduction* | | |
|---|---|---|---|
| | NOL01 | NOL02 | NOL03 |
| ZEA | 96.9 | 64.8 | 99.4 |
| FBI | 4.7 | 18.7 | 8.8 |
| OTA | 7.3 | 10.0 | 15.9 |
| T-2 | 7.2 | 1.0 | 4.2 |

*average of the % obtained over 3 samples

These results show, under aerobic conditions, a reducing capacity of NOL01 on ZEA, OTA and T-2, the effect observed on the last two mycotoxins nevertheless being lower. Likewise, they show a reducing capacity of NOL02 and NOL03 on ZEA, $FB_1$ and OTA, the observed effect on these last two mycotoxins nevertheless being lower.

8—Efficacy Test of the NOL01, NOL02 and NOL03 Bacteria in Combination

The inventors also conducted bacterial cultures according to the invention according to 1—in the presence of ZEA, $AFB_1$ and $FB_1$, in rich medium (TSB) or minimal medium re-enriched with $NO_3$ and glucose (MMNG), but with an inoculum containing 1 µg/mL of the three bacteria according to the invention NOL01, NOL02, NOL03 implemented in equal proportions.

TABLE 11

| | | | Percentage of reduction* at t = 72 h | | | |
|---|---|---|---|---|---|---|
| | | | NOL01 | NOL02 | NOL03 | POOL |
| Aerobic | TSB | ZEA | 96.9 | 64.8 | 99.4 | 100 |
| Anaerobic | MMNG | ZEA | 98.4 | 80.3 | 96.4 | Not tested |
| | | $AFB_1$ | 1.6 | 0.5 | 0.7 | 11.7 |
| | | $FB_1$ | 3.0 | 4.4 | 2.0 | 18.1 |

*average of the % obtained over 3 samples

These results show a capacity to reduce the presence of ZEA mycotoxins by the NOL01, NOL02 and NOL03 bacteria in combination, whether in aerobic conditions in rich medium (TSB), or in anaerobic conditions in minimal medium re-enriched with $NO_3$ and glucose (MMNG). An ability has also been noted to reduce the presence of $AFB_1$ and $FB_1$ of this pool under anaerobic conditions and MMNG medium, although it is more reduced.

9—Measure of Efficacy Against Metabolites of ZEA

The inventors verified the ability of strains NOL01, NOL02 and NOL03 according to the invention to reduce mycotoxins, according to 1—but on the metabolites of ZEA, under aerobic conditions in minimal medium (MM) and under anaerobic conditions in minimal medium re-enriched with $NO_3$ and glucose (MMNG).

TABLE 12

| | Percentage of reduction* at t = 72 h | | | | | |
|---|---|---|---|---|---|---|
| | Aerobic MM | | | Anaerobic MMNG | | |
| | NOL01 | NOL02 | NOL03 | NOL01 | NOL02 | NOL03 |
| ZEA | 100 | 98.9 | 99.0 | 100 | 96.3 | 96.3 |
| α-ZOL | 100 | 98.4 | 99.0 | 100 | 56.6 | 100 |
| β-ZOL | 100 | 96.6 | 99.0 | 100 | 47.0 | 100 |
| α-ZAL | 99.0 | 85.3 | 96.0 | 100 | 32.7 | 79.4 |
| β-ZAL | 98.9 | 80.0 | 93.0 | 100 | 44.5 | 87 |
| ZAL | 99.0 | 90.8 | 85.7 | 100 | 20.2 | 68.6 |

*average of the % obtained over 3 independent samples and standard deviation

These results confirm that irrespective of the culture conditions (presence or absence of oxygen, rich, re-enriched minimal or minimal medium), the bacteria according to the invention are capable of breaking down the ZEA as well as the metabolites thereof.

Example 2—In Vivo Test in Pigs

The inventors also tested the bacteria according to the invention under in vivo conditions in pigs in order to demonstrate their efficacy in animals.

1—Protocol

The inventors conducted a 21-day feeding test in an experimental station on 64 weaned piglets, divided into 2 tests, one on ZEA and the other on DON (or 32 piglets per test).

The following diets were applied for each of these tests (or 8 piglets per diet): (1) uncontaminated food without additive (2) uncontaminated food+additive (3) contaminated food without additive (4) contaminated food+additive For diets (3) and (4), the food distributed to the animal was artificially contaminated in an amount of 0.1 mg ZEA/kg of complete food at 12% moisture, or the maximum content recommended by European regulations according to Recommendation no. 2006/576/EC by the European Commission.

For the test on DON, the same 4 diets were applied, with an artificial contamination of the food distributed in an amount of 0.9 mg DON/kg of complete food at 12% moisture for diets (3) and (4).

The quantity of mycotoxins was analyzed at the beginning of the test and good homogeneity of the contamination of the distributed food was confirmed.

The additive as added corresponded to the combination of the 3 strains NOL01, NOL2 and NOL3 according to the invention implemented in equal proportions. This additive, in powdered form, was added to the food distributed after artificial contamination with mycotoxins and before distribution to the animals, and in sufficient quantity to reach $10^9$ bacterial colonies per kg of food.

About 1.5 kg of food is distributed per day per piglet.

The animals were distributed at 1 animal per metabolic cage for the test on ZEA, and 1 animal per pen for the test on DON.

An adaptation period of 3 weeks before launching the test diets was respected in order to avoid stressing the animals during the transition to post-weaning and to acclimate those who were in metabolic cages for the test on ZEA.

At the end of this 3-week adaptation period, the tests began and lasted 3 weeks (21 days).

2—Analyses and Zootechnical Parameters

The following specimens were collected throughout the test:

Blood samples at 0, 7, 14 and 21 days on all animals,
Collection of feces and urine between the $17^{th}$ and $21^{st}$ days for the test on ZEA,
Collection of feces at 21 days, at slaughter for the test on DON,
Collection of tissue samples at 21 days: liver, kidneys, muscles, reproductive organs, intestinal tracts.

On the collected samples, as a priority the samples collected at the end of the test, the following analyses were done:

Detection of ZEA and its metabolites α-zearalenol and β-zearalenol in the plasma, urine and feces collected on the animals from the ZEA test,
Detection of DON and its metabolites in the serum collected from the animals from the test on DON.

For both tests, the following zootechnical parameters were noted: body weight, average daily food consumption, mortality, morbidity. For the tests on ZEA, the following parameters were also noted: size of the vulva and/or degree of inflammation of the vulva, weight of the reproductive organs.

The invention is not limited to the described embodiments, and other embodiments will appear clearly to one skilled in the art.

The invention claimed is:

1. A method for the treatment of animals suffering from a pathology related to the ingestion of at least one mycotoxin, or the prevention of said pathologies, the method comprising a step of administering to an animal in need thereof, a composition comprising or consisting essentially of
   strain NOL03,
   said strain being filed with the CNCM under number CNCM I-4607.

2. The method according to claim 1, wherein said composition comprises said strain NOL03, and at least one of the following strains,
   Strain NOL01, filed with the CNCM under number CNCM I-4606,
   Strain NOL02, filed with the CNCM under number CNCM I-5043, and
   Strain NOL04, filed with the CNCM under number CNCM I-4608.

3. The method according to claim 1, wherein said pathologies are related to the ingestion of at least two mycotoxins with different structures.

4. The method according to claim 1, where wherein said composition comprises
   Strain NOL03 deposited with the CNCM under number CNCM I-4607,
   Strain NOL01 deposited with the CNCM under number CNCM I-4606, and
   Strain NOL02 deposited with the CNCM under number CNCM I-5043.

5. The method according to claim 1, wherein said at least one mycotoxin is chosen from aflatoxins B1, B2, M1, G1 and G2, toxin T-2, toxin HT-2, deoxynivalenol (or nivalenol), zearalenone, a fumonisin B family mycotoxin, and ochratoxin A.

6. The method according to claim 5, wherein said fumonisin B family mycotoxin is fumonisin B1.

7. The method according to claim 3, wherein said at least two mycotoxins comprise deoxynivalenol (DON) and a fumonisin B family mycotoxin.

8. The method according to claim 4, wherein said at least one mycotoxin is selected from deoxynivalenol (DON) and a fumonisin B family mycotoxin.

9. The method according to claim 8, wherein said fumonisin B family mycotoxin is fumonisin B1.

\* \* \* \* \*